United States Patent [19]

Meyer et al.

[11] 4,360,679
[45] Nov. 23, 1982

[54] BENZOFURANYL-BENZIMIDAZOLES

[75] Inventors: Hans R. Meyer, Binningen; Kurt Weber, Basel, both of Switzerland

[73] Assignee: Ciba-Geigy Corporation, Ardsley, N.Y.

[21] Appl. No.: 192,576

[22] Filed: Sep. 30, 1980

Related U.S. Application Data

[62] Division of Ser. No. 972,139, Dec. 21, 1978, Pat. No. 4,250,317, which is a division of Ser. No. 815,889, Jul. 15, 1977, Pat. No. 4,146,725.

[30] Foreign Application Priority Data

Jul. 26, 1976 [LU] Luxembourg ............................ 75458
Apr. 27, 1977 [LU] Luxembourg ........................ 77216

[51] Int. Cl.³ .................. C07D 405/04; C07D 405/14
[52] U.S. Cl. ......................................... 548/327; 8/927
[58] Field of Search ........................................ 548/327

[56] References Cited
U.S. PATENT DOCUMENTS

| | | | |
|---|---|---|---|
| 3,637,734 | 1/1972 | Harnisch et al. | 548/327 |
| 3,772,323 | 11/1973 | Schläpfer et al. | 548/327 |
| 3,931,215 | 1/1976 | Horn et al. | 548/327 |
| 3,940,417 | 2/1976 | Schläpfer | 548/327 |
| 4,001,138 | 1/1977 | Lohmann | 548/327 |

Primary Examiner—Henry R. Jiles
Assistant Examiner—N. Harkaway
Attorney, Agent, or Firm—Edward McC. Roberts

[57] ABSTRACT

Novel benzofuranyl benzimidazoles of the formula

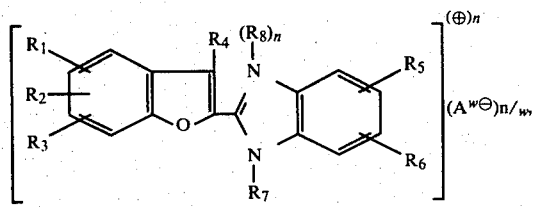

wherein
$R_1$ represents a hydrogen atom, an alkenyloxy or cycloalkyloxy radical, an unsubstituted or substituted alkoxy, phenylalkoxy or phenoxy radical, each of
$R_2$ and $R_3$ independently represents a hydrogen atom, an alkyl or alkoxy radical, a halogen atom, or, if $R_1$ represents hydrogen, together in the ortho-position to each other they represent a radical of the formula $-CH=CH-CH=CH-$, $-O-CH_2-O-$ or $-O-CH_2-CH_2-O-$,
$R_4$ represents a hydrogen atom, an alkyl, alkoxy or phenyl radical,
$R_5$ represents a sulpho or carboxyl group or the functional derivatives thereof including the cyano group or the trifluoromethyl group,
$R_6$ represents a hydrogen or halogen atom, an alkyl or alkoxy radical,
$R_7$ represents a cycloalkyl, alkenyl, or unsubstituted or substituted alkyl, phenyl or phenylalkyl radical, or, if n is 0, also represents a hydrogen atom,
$R_8$ represents a hydrogen atom, a cycloalkyl, alkenyl, or unsubstituted or substituted alkyl or phenylalkyl radical,
$A^{w\ominus}$ represents a colorless anion of an inorganic or organic acid and
w represents the valency of the anion A, and
n is 0 or 1, their preparation as well as their use as optical brighteners are disclosed.

5 Claims, No Drawings

BENZOFURANYL-BENZIMIDAZOLES

This is a division of application Ser. No. 972,139 filed on Dec. 21, 1978, now U.S. Pat. No. 4,250,317, issued Feb. 10, 1981, which is a division of Ser. No. 815,889, filed on July 15, 1977 now U.S. Pat. No. 4,146,725, issued Mar. 27, 1979.

The present invention relates to novel benzofuranyl-benzimidazoles, to a process for their manufacture and to the used thereof for optically brightening organic material.

Quaternised benzofuranyl-benzimidazoles and the use thereof as fluorescent brighteners are known from DOS Nos. 2,031,774 and 2,159,469. Surprisingly, it has now been found that benzofuranyl-benzimidazoles which are substituted in a specific manner are particularly advantageous.

The novel benzofuranyl-benzimidazoles have the formula

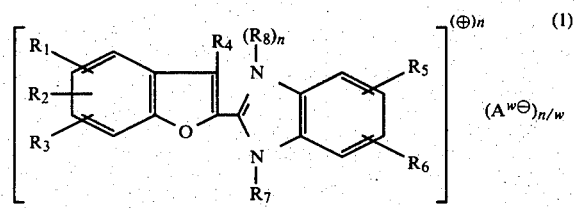

wherein
$R_1$ represents a hydrogen atom, an alkenyloxy or cycloalkyloxy radical, an unsubstituted or substituted alkoxy, phenylalkoxy or phenoxy radical, each of
$R_2$ and $R_3$ independently represents a hydrogen atom, an alkyl or alkoxy radical, a halogen atom, or, if $R_1$ represents hydrogen, together in the ortho-position to each other they represent a radical of the formula $-CH=CH-CH=CH-$, $-O-CH_2-O-$ or $-O-CH_2-CH_2-O-$,
$R_4$ represents a hydrogen atom, an alkyl, alkoxy or phenyl radical,
$R_5$ represents a sulpho or carboxyl group or the functional derivatives thereof including the cyano group or the trifluoromethyl group,
$R_6$ represents a hydrogen or halogen atom, an alkyl or alkoxy radical,
$R_7$ represents a cycloalkyl, alkenyl, or unsubstituted or substituted alkyl, phenyl or phenylalkyl radical, or, if n is 0, also represents a hydrogen atom,
$R_8$ represents a hydrogen atom, a cycloalkyl, alkenyl, or unsubstituted or substituted alkyl or phenylalkyl radical,
$A^{w\ominus}$ represents a colourless anion or an inorganic or organic acid and
w represents the valency of the anion A, and
n is 0 or 1.

The term "a halogen atom" is to be understood as meaning a fluorine, chlorine and bromine and, preferably, a chlorine atom.

Examples of functional derivatives of the sulpho or carboxyl group are esters, amides and salts. Particularly preferred esters of sulphonic acid are the aromatic esters. In addition, the cyano group is to be mentioned as derivative of the carboxyl group.

A suitable anion $A^{w\ominus}$ is any colourless anion of an organic or inorganic acid. Its nature has no material influence on the brightening properties of the compounds of the invention. The anion is normally introduced by means of the process of manufacture (quaternisation or protonisation); but it can also be replaced by another anion by known methods (see for example Houben-Weyl, Methoden der organischen Chemie, Vol. XI/2, pp. 620–626). In accordance with DOS No. 2,549,436, halogen anions can also be replaced by anions of aliphatic carboxylic acids by reacting the halide in the presence of these carboxylic acids using epoxides as hydrogen halide acceptors.

In compounds of the formula (1), in which one of the substituents represents the group $-SO_3H$, the strongly acid sulpho group can form an inner salt with the basic imidazole ring. The group $SO_3^{\ominus}$ as one of the substituents of the benzimidazole ring can thus also act as anion $A^{\ominus}$ in quaternised or protonised compounds of the formula (1).

Compounds to be highlighted within the scope of the benzofuranyl-benzimidazoles of the formula (1) are those of the formula

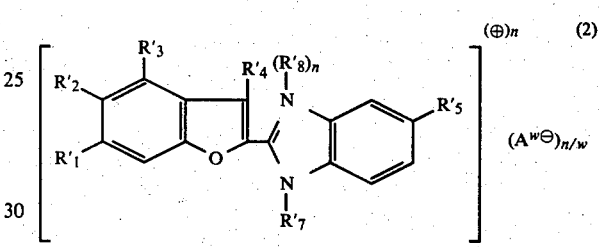

wherein
$R_1'$ represents an alkoxy radical of 1 to 12 carbon atoms, an alkenyloxy radical of 3 or 4 carbon atoms, a phenoxy or phenylalkoxy radical containing 1 to 4 carbon atoms in the alkoxy moiety which is unsubstituted or substituted in the phenyl moiety by chlorine, alkyl or alkoxy, each of 1 to 4 carbon atoms, or represents a hydroxyalkoxy, alkoxyalkoxy, cyanoalkoxy, carbalkoxyalkoxy, carbamoylalkoxy or cyclohexyloxy radical or represents hydrogen if $R_2'$ and $R_3'$ together form the butadienylene radical, or together with $R_2'$ forms the methylenedioxy or ethylenedioxy radical,
$R_2'$ represents a hydrogen or halogen atom, an alkyl or alkoxy radical, each of 1 to 4 carbon atoms, or, if $R_1'$ represents hydrogen, together with $R_3'$ forms the butadienylene radical, or together with $R_1'$ forms the methylenedioxy or ethylenedioxy radical,
$R_3'$ represents a hydrogen atom, an alkyl or alkoxy radical, each of 1 to 4 carbon atoms, or, if $R_1'$ represents hydrogen, together with $R_2'$ forms the butadienylene radical,
$R_4'$ represents hydrogen, alkyl or alkoxy, each of 1 to 4 carbon atoms, or phenyl,
$R_7'$ represents alkyl of 1 to 8 carbon atoms, alkenyl of 3 to 4 carbon atoms, cyclohexyl, hydroxyalkyl of 2 to 4 carbon atoms, alkoxyalkyl of altogether 3 to 6 carbon atoms, carboxyalkyl of 2 to 5 carbon atoms, carbalkoxyalkyl of altogether 3 to 9 carbon atoms, cyanoalkyl of 2 to 5 carbon atoms, benzyl which is unsubstituted or substituted by chlorine, methyl or methoxy, dialkylaminoalkyl of altogether 3 to 7 carbon atoms or phenethyl, or, if n is 0, also represents hydrogen, R$_8'$ represents hydrogen, alkyl of 1 to 6 carbon atoms, hydroxyalkyl of 2 to 4 carbon atoms, cyanoalkyl of 2 to 5 carbon atoms, carboxyalkyl of 2 to 5 carbon atoms, carbamoylalkyl of 2 to 6 carbon atoms, alkoxycarbonylalkyl of altogether 3 to 9 carbon atoms, alkenyl of 3 or 4 carbon atoms, or benzyl which is unsubstituted or substituted by chlorine, methoxy or methyl, R$_5'$ represents sulpho or the salts thereof, phenoxysulphonyl which is unsubstituted or mono- or tri-substituted by alkyl of 1 to 4 carbon atoms, chlorine or methoxy; or represents cyano, trifluoromethyl, —COOY$_1$—, SO$_2$NY$_1$Y$_2$ or —CONY$_1$Y$_2$, wherein Y$_1$ represents hydrogen, alkyl of 1 to 8 carbon atoms, alkenyl of 3 to 4 carbon atoms, alkoxyalkyl of altogether 3 to 6 carbon atoms, phenoxyalkyl of altogether 7 to 9 carbon atoms, carboxyalkyl of 2 to 6 carbon atoms, carbalkoxyalkyl of altogether 3 to 6 carbon atoms, cyanoalkyl of 2 to 5 carbon atoms, benzyl which is unsubstituted or substituted by methyl, chlorine or methoxy, phenyl which is unsubstituted or substituted by chlorine, methyl or methoxy, dialkylaminoalkyl of altogether 3 to 7 carbon atoms or phenethyl, and in the group —COOY$_1$ also represents a salt-forming cation, Y$_2$ represents hydrogen, alkyl of 1 to 4 carbon atoms, alkenyl of 3 or 4 carbon atoms or hydroxyalkyl of 2 to 4 carbon atoms, or Y$_1$ and Y$_2$ together with the nitrogen atom to which they are attached represent a 5- or 6-membered saturated heterocyclic ring which can contain one or two additional heteroatoms and can also be substituted by alkyl radicals, n is 0 or 1, A$^{w\ominus}$ represents a colourless anion and w represents the valency of the anion A.

Suitable alkyl or alkoxy radicals are in particular those containing 1 to 8 carbon atoms. Preferred lower alkyl and alkoxy radicals are those containing 1 to 4 carbon atoms. The same limits apply to the individual moieties in groups composed of these radicals (for example lower alkoxy-lower alkyl).

Possible 5- or 6-membered heterocyclic rings which are formed by Y$_1$ and Y$_2$ together with the nitrogen atom to which they are attached are preferably saturated rings wherein either the nitrogen atom can be the only heteroatom or which can contain one or two further heteroatoms, preferably nitrogen and/or oxygen atoms. The pyrrolidine, piperidine, imidazolidine, pyrazolidine, piperazine, morpholine and oxalidine ring may be mentioned as examples. These heterocyclic rings can carry substituents, for example lower alkyl groups.

As salt-forming cations, particularly mention is to be made of alkali metal, ammonium or amine ions. Alkali metal ions are preferred.

Compounds within the scope of formula (1) which are deserving of particular mention are those of the formula

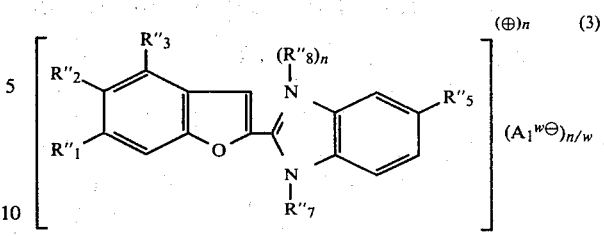

(3)

wherein

R$_1''$ represents an alkoxy radical of 1 to 8 carbon atoms, an alkenyloxy radical of 3 to 4 carbon atoms, a benzyloxy or phenoxy radical, an alkoxyalkoxy radical of altogether 3 to 6 carbon atoms or represents a hydrogen atom if R$_2''$ and R$_3''$ together represent the butadienylene radical, R$_2''$ represents a hydrogen or chlorine atom or, if R$_1''$ represents hydrogen, together with R$_3''$ represents the butadienylene radical, R$_3''$ represents a hydrogen atom or together with R$_2''$ represents the butadienylene radical, R$_5''$ represents phenoxysulphonyl which is unsubstituted or substituted by methyl, chlorine or methoxy; cyano, trifluoromethyl, —COOY, —SO$_2$NY$_1'$Y$_2'$ or —CONY$_1'$Y$_2'$, wherein Y$_1'$ represents hydrogen, alkyl of 1 to 8 carbon atoms, alkenyl of 3 or 4 carbon atoms, cyclohexyl, hydroxyalkyl of 2 or 4 carbon atoms, alkoxyalkyl of altogether 3 to 6 carbon atoms, phenoxyalkyl of altogether 7 to 9 carbon atoms, carbalkoxyalkyl of altogether 3 to 6 carbon atoms, cyanoalkyl of 2 or 3 carbon atoms, benzyl or dialkylaminoalkyl of altogether 3 to 7 carbon atoms, Y$_2'$ represents hydrogen, alkyl of 1 to 4 carbon atoms, alkenyl of 3 or 4 carbon atoms or hydroxyalkyl of 2 to 4 carbon atoms, and Y has the meaning of Y$_1'$ and additionally represents phenyl or an alkali metal ion or Y$_1'$ and Y$_2'$ together with the nitrogen atom to which they are attached represent a piperidine, pyrrolidine or a morpholine ring which is unsubstituted or substituted by one or two methyl radicals, R$_7''$ represents alkyl of 1 to 6 carbon atoms, alkenyl of 3 or 4 carbon atoms, cyclohexyl, hydroxyalkyl of 2 to 4 carbon atoms, alkoxyalkyl of altogether 3 to 6 carbon atoms, carbalkoxyalkyl of altogether 3 to 6 carbon atoms or benzyl, and, if n is 0, also represents hydrogen, R$_8''$ represents hydrogen, alkyl of 1 to 4 carbon atoms which is unsubstituted or substituted by hydroxy, cyano, carboxy, alkoxycarbonyl of 2 to 4 carbon atoms or carbamoyl, or represents alkenyl of 3 or 4 carbon atoms or benzyl, n is 0 or 1, A$^{w\ominus}$ represents a halide, formiate, acetate, lactate, CH$_3$SO$_4^\ominus$, C$_2$H$_5$SO$_4^\ominus$, C$_6$H$_5$SO$_3^\ominus$, p-CH$_3$-C$_6$H$_4$SO$_3^\ominus$, p-Cl-C$_6$H$_4$SO$_3^\ominus$, carbonate or bicarbonate and w represents the valency of the anion A$_1$.

Particularly interesting compounds are those of the formula

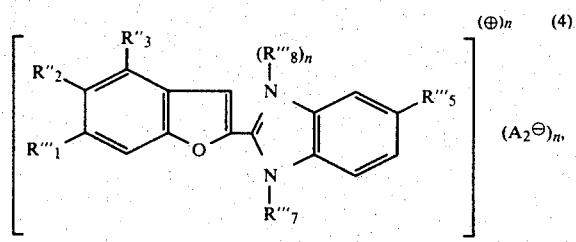

wherein
- $R_1'''$ represents an alkoxy radical of 1 to 4 carbon atoms or, if $R_2''$ and $R_3''$ together represent the butadienylene radical, represents a hydrogen atom,
- $R_2''$ represents a hydrogen or chlorine atom or together with $R_3''$ represents the butadienylene radical if $R_1'''$ represents hydrogen,
- $R_3''$ represents a hydrogen atom or together with $R_2''$ represents the butadienylene radical if $R_1'''$ represents hydrogen,
- $R_5'''$ represents cyano or trifluoromethyl, phenoxysulphony, a group of the formula —COOY′, —SO$_2$NY$_1''$Y$_2''$ or —CONY$_1''$Y$_2'''$, wherein Y′ represents hydrogen, an alkali metal ion or alkyl of 1 to 6 carbon atoms, Y$_1''$ represents hydrogen, alkyl of 1 to 6 carbon atoms, dialkylaminoalkyl of altogether 3 or 7 carbon atoms or alkoxyalkyl of altogether 3 to 6 carbon atoms, cyclohexyl, benzyl or alkenyl of 3 or 4 carbon atoms, Y$_2''$ represents hydrogen, alkyl of 1 to 4 carbon atoms, or Y$_1''$ and Y$_2''$ together with the nitrogen atom to which they are attached represent a morpholine ring,
- $R_7'''$ represents alkyl of 1 to 6 carbon atoms or benzyl,
- $R_8'''$ represents hydrogen, alkyl of 1 to 4 carbon atoms, carbalkoxy of altogether 3 to 5 carbon atoms or benzyl,
- $A_2^\ominus$ represents a halogen ion or a methylsulphate, ethylsulphate or p-tolylsulphonate ion, and
- n is 0 or 1, including also the compounds of the formula

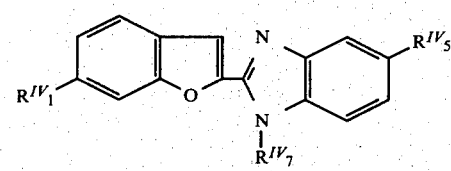

wherein
- $R_1'^v$ represents alkoxy of 1 to 4 carbon atoms,
- $R_7'^v$ represents alkyl of 1 to 4 carbon atoms, alkoxyalkyl of altogether 3 to 6 carbon atoms or benzyl, and
- $R_5'^v$ represents cyano, trifluoromethyl, phenoxysulphonyl, a group of the formula —COOY′, —SO$_2$NHY$_1'''$, or —CONHY$_1'''$, wherein Y′ represents hydrogen, an alkali metal ion or alkyl of 1 to 6 carbon atoms and Y$_1'''$ represents hydrogen, alkyl of 1 to 6 carbon atoms, dialkylaminoalkyl of altogether 3 to 7 carbon atoms or alkoxyalkyl of altogether 3 to 6 carbon atoms, hydroxyalkyl of 2 to 4 carbon atoms, cyclohexyl or benzyl.

Particularly preferred compounds are the quaternised benzofuranyl-benzimidazoles of the formula

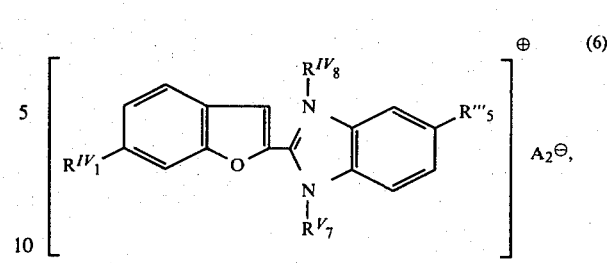

wherein
- $R_1'^v$ represents alkoxy of 1 to 4 carbon atoms,
- $R_7'^v$ represents alkyl of 1 to 6 carbon atoms or benzyl, and
- $R_8'^v$ represents hydrogen, alkyl of 1 to 4 carbon atoms, carbalkoxyalkyl of altogether 3 to 6 carbon atoms or benzyl, and
- $R_5'''$ and $A_2^\ominus$ are as defined in formula (4).

The process of the present invention for the manufacture of the compounds of the formula (1) and of the subformulae (2) to (6) comprises acylating an o-phenylene-diamine of the formula

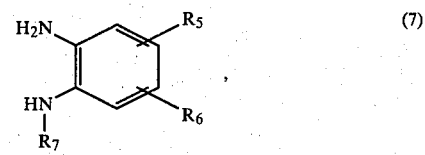

wherein $R_5$, $R_6$ and $R_7$ have the meanings given in formula (1), with a compound of the formula

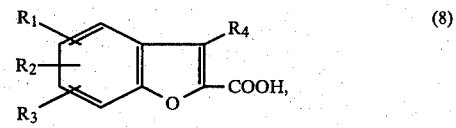

wherein $R_1$, $R_2$, $R_3$ and $R_4$ have the meanings given in formula (1), or with a functional derivative thereof, and effecting cyclisation, preferably in the presence of an acid condensation agent, for example acetic acid, hydrogen chloride, boric acid, zinc chloride, polyphosphoric acid, phosphoric acid or p-toluenesulphonic acid, and optionally quaternising the resultant compound of the formula (1), wherein n is 0, by reaction with an alkylating agent, or protonising it with an acid.

Compounds of the formula (1), wherein n is 0 (non-quaternised compounds), are also obtained by reacting compounds which are unsubstituted at the imidazole ring of the formula (1), wherein $R_7$ represents hydrogen and n is 0, with alkylating agents in the presence of basic compounds by known methods.

By functional derivatives of the carboxylic acids of the formula (8) are meant salts, halides, esters, amines, iminoethers and nitriles.

The manufacture of the acid addition products (compounds of the formula (1) wherein $R_8$ is hydrogen and n is 1) or of the quaternary ammonium salts, viz. the reaction of compounds of the formula (1), wherein n is 0, with a protonising or quaternising agent of the formula $R_8$-A, wherein $R_8$ has the above meaning and A represents the radical which is converted into the anion $A^{w\ominus}$ during the quaternisation or protonisation, can be carried out in the conventional manner, preferably in a solvent, and advantageously using at least one molar equivalent of the protonising or quaternising agent.

If it is desired to manufacture compounds of the formula (1) which are quaternised with alkyl radicals, then the alkylating agent used is preferably a dialkyl sulphate, such as dimethyl and diethyl sulphate, an alkyl halide, such as methyl chloride, ethyl, propyl and butyl iodide or ethyl, propyl and butyl bromide, allyl chloride or allyl bromide, crotyl chloride or crotyl bromide as well as alkylbenzenesulphonates, such as p-methyl-, ethyl- or chlorobenzenesulphonates. If it is desired to manufacture compounds of the formula (1) which are quaternised with a benzyl radical, then preferably a benzyl halide, such as benzyl chloride, is used for the benzylation. Examples of further quaternising agents are $BrCH_2CH_2OH$, $BrCH_2CHOHCH_3$, haloacetic acid derivatives, such as $ClCH_2CO_2CH_2CH_3$, $BrCH_2COOH$, $BrCH_2COOCH_3$, $ClCH_2CN$, $ClCH_2CONH_2$, $ClCH_2CONHCH_3$ and $ClCH_2CON(CH_3)_2$ and also ethylene oxide or propylene oxide in the presence of suitable anions, for example of formic, acetic or lactic acid.

If protonised compounds of the formula (1) are desired, i.e. acid addition salts thereof (in which $R_8$ is hydrogen and n is 1), then mineral acids in particular are used as protonising agents. Suitable protonising agents are in general all strong to medium strong organic acids or mineral acids in which the anions can be exchanged by double reaction. The desired acid is added dropwise for example, with stirring, to a solution of the benzimidazole, whereupon the salt precipitates. Gaseous acids, for example hydrogen chloride, are introduced.

Suitable solvents in which the protonisation or quaternisation can be carried out are in general all inert solvents. Preferred solvents are those which dissolve the starting material and from which the end product precipitates immediately. Examples of such solvents are: aromatic hydrocarbons, such as benzene, toluene and xylene; halogenated hydrocarbons, such as trichloroethane, tetrachloroethylene, chlorobenzene or dichlorobenzene, and also nitrobenzene; alkanols and open or cyclic ethers, such as butanol, dibutyl ether, ethylene glycol monomethyl ether, ethylene glycol monoethyl ether, anisole or dioxane; ketones, such as cyclohexanone or methyl ethyl ketone; fatty acid amides, such as dimethyl formamide or dimethyl acetamide; sulphoxides, such as dimethyl sulphoxide; and carboxylates, such as ethyl acetate or butyl acetate. The reaction is carried out for example at temperatures between 60° and 180° C., preferably between 90° and 140° C. On occasion it is also advantageous to use an excess of alkylating agent as solvent.

The starting materials of the formula (7) are prepared in a manner known per se by reaction of o-chloro-nitrobenzene derivatives with primary amines or ammonia to give the correspondingly substituted o-nitroanilines and reduction of these latter, for example by means of catalytic hydrogenation (cf. Belgian Pat. No. 595,327, DOS Nos. 2,239,614 and 1,522,412). o-Nitroanilines with substituents which can be readily hydrogenated catalytically, for example allyl groups, are more expediently reduced with sodium hydrogen sulphite or iron (Bechamp method).

The starting compounds of the formula (8) are known or they can be obtained by methods which are known per se.

Alternatively, the compounds of the formula (1) can also be manufactured by acylating a correspondingly substituted o-nitroaniline with correspondingly substituted cumarilic acid or a functional derivative thereof, reducing the nitro group in acid medium, for example with stannous chloride, and simultaneously effecting the cyclisation to give the imidazole ring.

The novel compounds defined above exhibit a more or less pronounced fluorescence in the dissolved or finely divided state. They can be used for optically brightening a wide variety of synthetic, regenerated man-made or natural organic materials or substances which contain organic materials.

Without any restriction being implied by the following classification, examples of organic materials which can be optically brightened are:

I. Synthetic materials of high molecular weight:
  (a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylic esters, acrylic acid, acrylonitrile, acrylic amides and their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);
  (b) polymerisation products which can be obtained by ring opening, for example, polyamides of the polycaprolactam type, and also polymers which are obtained both by polyaddition and by polydondensation, for example polyethers or polyacetals;
  (c) polycondensation products or precondensates based on bifunctional or polyfunctional compounds with condensable groups, their homocondensation and co-condensation products, and aftertreatment products, for example polyesters, especially saturated polyesters (for example ethylene glycol terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;
  (d) polyaddition products, such as polyurethanes (crosslinked and uncrosslinked) and epoxide resins.

II. Regenerated man-made organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominently two-dimensional structures, such as films, foils, lacquers, coatings and impregnations or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperature of 20° to 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermofixation application, or exhaustion dyeing processes in dyeing machines).

The fluorescent brighteners of the present invention can further be added to, or incorporated in, the materials before or during their shaping. Thus they can for example be added to the compression moulding composition or injection moulding composition during the manufacture of films, sheets (for example incorporated in polyvinyl chloride in a roller mill at elevated temperature) or mouldings.

If the fashioning of man-made synthetic or regenerated man-made organic materials is effected by spinning processes or from spinning solutions/melts, the fluorescent brighteners can be applied by the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

Most preferably the fluorescent brighteners of the formulae (1) to (6) are applied to the fibres prepared by the wet spinning process while these are still in the gel state. In the gel state the fibres still contain large amounts of water and are therefore highly swelled. After the fibre formation (spinning) and the washing procedure to remove solvents or solubilisers, the fibres are stretched to orientate the macromolecules and subsequently dried, thereby losing the gel state.

Methods of optically brightening polyacrylonitrile fibres in the gel state consist substantially in bringing the fibres in the swelled state into contact with the brightener solution either on a pad or in a bath. The bath treatment can also be carried out in such a manner that the fibres or filaments are agitated through a brightener suspension or solution flowing in countercurrent. The baths are advantageously so prepared that the brightener is dissolved or dispersed in water and the resultant liquor is adjusted to the desired pH values with acid and/or a buffer salt. This pH value is normally between 1 and 7, for example between 1.5 and 5.5. The concentration of brightener in the bath is generally so chosen that, after the treatment, 0.005 to 0.5%, for example 0.05 to 0.2%, of fluorescent brightener, referred to the dry weight of the fibres, has exhausted onto the fibres. The treatment of the fibres in the bath can be carried out at a bath temperature below 50° C., for example between 10° and 30° C. In general, the duration of the treatment of the fibres in the brightener bath is less than 2 minutes, preferably less than 40 seconds.

The present invention accordingly also relates to the use of the fluorescent brighteners of the formulae (1) to (6) for application to polyacrylonitrile fibres which are in the gel state.

The fluorescent brighteners of the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft handle finishes, antisoiling finishes or antistatic finishes, or antimicrobial finishes;

(d) incorporation of the fluorescent brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

(e) as additives to master batches;

(f) as additives to a wide variety of industrial products in order to render these more marketable (for example improving the appearance of soaps, detergents, pigments);

(g) in combination with other optically brightening substances;

(h) in spinning bath preparations, that is to say as additives to spinning baths which are used for improving the slip for the further processing of synthetic fibres, or from a special bath before the stretching of the fibre;

(i) as scintillators for various purposes of a photographic nature, for example for electrophotographic reproduction or supersensitising;

(j) depending on the substitution as laser dyes.

If the brightening process is combined with textile treatment or finishing methods, the combined treatment can in many cases advantageously be carried out with the aid of appropriate stable preparations which contain the fluorescent brightener compounds in such a concentration that the desired brightening effect is achieved.

In certain cases, the fluorescent brighteners are made fully effective by an aftertreatment. This can be, for example, a chemical treatment (for example acid treatment), a thermal treatment (for example heat) or a combined chemical/thermal treatment. Thus, for example, the appropriate procedure to follow in brightening a number of fibre substrates, for example polyester fibres, with the fluorescent brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperature between 120° and 225°0 C., for example by heating in a drying chamber, by ironing within the specified temperature range or by treatment with dry, superheated steam. The drying and dry heat treatment can also be carried out in immediate succession or be combined in a single process stage.

The amount of fluorescent brightener of the present invention to be used, referred to the weight of the material to be brightened, can vary within wide limits. A marked and lasting effect can be obtained even with very insignificant amounts, in certain cases 0.0001 percent by weight. But it is also possible to use amounts of up to app. 0.8 percent by weight and, on occasion, up to app. 2 percent by weight. For most practical purposes, it is preferable to use amounts between 0.005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent brighteners of this invention are also particularly suitable for use as additives to wash liquors or heavy duty and domestic detergents, to which they can be added in various ways. They are appropriately added to wash liquors in the form of their solutions in water or organic solvents, or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brightening agents can be mixed, kneaded or ground with the active detergents and, in this form, admixed with the finishing powder. However, they can also be sprayed in a dissolved or pre-dispersed form on the finished detergent.

Suitable detergents are the known mixtures of active detergents, for example soap in the form of chips and powders, synthetics, soluble salts of sulphonic acid hemiesters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerol sulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colourants.

The novel fluorescent brighteners especially the quaternised ones, have the particular advantage that they are also active in the presence of active chlorine donors, for example, hypochlorite, and can be used without significant loss of effect in wash liquors containing nonionic washing agents, for example alkylphenolglycol ethers.

The compounds according to the invention are added in amounts of 0.005 to 1% or more, based on the weight of the liquid or pulverulent finished detergent. Wash liquors which contain the indicated amounts of the claimed fluorescent brighteners impart a brilliant appearance in daylight when used to wash textiles made from cellulose fibres, polyamide fibres, cellulose fibres with a high quality finish, polyester fibres or wool.

The washing treatment is carried out as follows, for example:

The textiles are treated for 1 to 30 minutes at 20° to 100° C. in a wash liquor which contains 1 to 10 g/kg of a built-up composite detergent and 0.05 go 1%, based on the weight of the detergent, of the claimed brightening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

Particularly good effects are obtained with the fluorescent brighteners of the present invention when using polyacrylonitrile and modified polyester as substrates. The fluorescent brighteners, especially the quaternised compounds of the formula (1), are exceedingly resistant to chlorites.

The use of the fluorescent brighteners of the invention for brightening polyacrylonitrile fibres in the gel state is particularly worthy of mention.

In the following Examples, parts and percentages are always by weight, unless otherwise stated. Unless indicated to the contrary, melting points and boiling points are uncorrected.

EXAMPLE 1

With stirring, 9 g of anhydrous sodium acetate are added to 21.5 g of 4-methylamino-3-aminobenzene-methylsulphonamide in 150 ml of glacial acetic acid and then 24.1 g of pulverised 6-methoxycumarilyl chloride are added in portions. The reaction mixture is stirred for 1½ hours at room temperature and then for a further 3 hours under reflux. After cooling, the reaction mixture is diluted with 150 ml of water and the precipitated product is collected by filtration, repeatedly washed with water and dried at 100° C. in vacuo, affording 34.3 g (92% of theory) of the compound of the formula

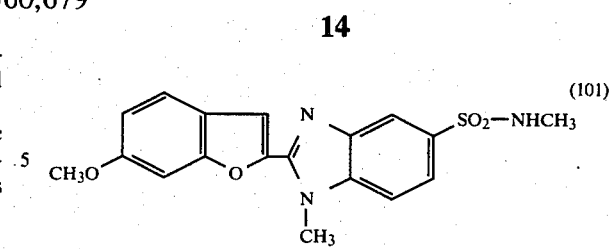
(101)

Purification is effected by recrystallisation from o-dichlorobenzene with the aid of fuller's earth and extraction by boiling with ethanol, giving almost colourless crystals with a melting point of 243° C.

In similar manner the compounds of the general formula (102) described in Table II are obtained from 6-methoxycumarilyl chloride and the o-phenylenediamines listed in Table I. Table I also indicates the melting points of the corresponding o-nitroaniline compounds required for obtaining (by reduction) the o-phenylenediamines.

TABLE I

| $R_5$ | $R_7$ | melting point (°C.) NO₂/R₇—NH / R₅ | NH₂/R₇—NH / R₅ |
|---|---|---|---|
| —SO₂—NHCH₃ | —CH₃ | 181 | 103 |
| —COOH | —CH₃ | 310 | 197 decomposition |
| —COOCH₃ | —CH₃ | 145 | 102 |
| —SO₂—N(CH₃)₂ | —CH₃ | 152 | 159 |
| —SO₃Na | —CH₃ | 324 | 290 decomposition |
| —CN | —CH₃ | 168 | 140 |
| —SO₂—N(C₂H₅)(C₆H₅) | —CH₃ | 142 | 105 |
| —COOH | —C₂H₅ | 234 | 194 decomposition |
| —CO—NHCH₃ | —CH₃ | 206 | 155 |
| —SO₂NH₂ | —CH₃ | 213 | 171 |
| —COOC₂H₅ | —CH₃ | 101 | 88 |
| —SO₂OC₆H₅ | —CH₃ | 101 | 110* |
| —SO₂—NHCH₂CH₂OH | —CH₂CH₂OH | 158 | 95 |
| —SO₂—N(CH₂CH₂OH)₂ | —CH₃ | 150 | 151 |
| —SO₂—NH(CH₂)₃—N(CH₃)₂ | —CH₃ | 115 | 99 |
| —SO₂N(morpholino) | —CH₃ | 198 | 226 |
| —SO₃Na | —n-C₄H₉ | 300 (decomposition) | 296 (decomposition) |
| —SO₂—N(CH₃)₂ | —C₆H₅ | 128 | 113 (crude) |
| —SO₂—N(CH₃)₂ | —CH₂C₆H₅ | 157 | 195 |
| —SO₂—NHC₂H₅ | —C₂H₅ | 172 | 101 |
| —SO₂NH—C₆H₅ | —C₆H₅ | 166 | 191 |
| —SO₂NH₂ | —CH₂C₆H₅ | 190 | 154 |
| —SO₂NHCH₃ | —n-C₄H₉ | 136 | 80 |
| —CF₃ | —CH₃ | 74 | 50 |
| —SO₂NH—CH₂CH₂—OCH₃ | —CH₂CH₂—OCH₃ | 104 | 94 |
| —SO₂NH—CH₂CH═CH₂ | —CH₂CH═CH₂ | 86 | liquid (crude) |
| —SO₂NH₂ | —n-C₄H₉ | 178 | 116 |
| —SO₂NH—C₆H₅ | —CH₃ | 182 | 152 |
| —COOH | —CH₂—C₆H₅ | 208 | 204 |

TABLE I-continued melting point (°C.)

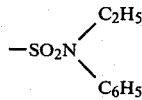

| $R_5$ | $R_7$ | $NO_2$/$R_7$-NH structure | $NH_2$/$R_7$-NH structure |
|---|---|---|---|
| —$SO_2$—NH—$CH_2CH_2$—$OCH_3$ | —$CH_3$ | 103 | liquid (crude) |
| —$SO_2$—$NHCH_3$ | —$CH_2$—$C_6H_5$ | 163 | 109 |
| —$CONH_2$ | —$CH_2$—$C_6H_5$ | 200 | 186 |
| —$SO_2NHCH_2C_6H_5$ | —$CH_2$—$C_6H_5$ | 135 | 141 |
| —$SO_2OC_6H_5$ | —$CH_2$—$C_6H_5$ | 125 | 139 |
| —$SO_2NH_2$ | —$C_2H_5$ | 157 | 168 |
| —$CF_3$ | —$CH_2$—$C_6H_5$ | 80 | 94 |
| —$SO_2OC_6H_4$—o-$CH_3$ | —$CH_3$ | 101 | 110 |
| —$SO_2OC_6H_5$ | —$C_2H_5$ | 104 | 114 |

*melting point of the hydrochloride: 185° C. (decomposition)

TABLE II

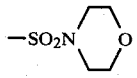

(102)

| formula | $R_5$ | $R_7$ | melting point (°C.) |
|---|---|---|---|
| (103) | —COOH | —$CH_3$ | 284 |
| (104) | —$SO_2N(CH_3)_2$ | —$CH_3$ | 192 |
| (105) | —$COOC_2H_5$ | —$CH_3$ | 203 |
| (106) | —$SO_2NH_2$ | —$CH_3$ | 339 (decomposition) |
| (107) | —$CONHCH_3$ | —$CH_3$ | 251 |
| (108) | —COOH | —$C_2H_5$ | 269 |
| (109) | —$COOCH_3$ | —$CH_3$ | 199 |
| (110) | —$SO_2N(C_2H_5)(C_6H_5)$ | —$CH_3$ | 181 |
| (111) | —CN | —$CH_3$ | 227 |
| (112) | —$SO_3H$ | —$CH_3$ | 360 |
| (113) | —$SO_2OC_6H_5$ | —$CH_3$ | 164 |
| (114) | —$SO_2NH$—$CH_2CH_2OH$ | —$CH_2CH_2OH$ | 240 |
| (115) | —$SO_2NH(CH_2)_3N(CH_3)_2$ | —$CH_3$ | 217 |

| formula | $R_5$ | $R_7$ | melting point (°0) |
|---|---|---|---|
| (116) | —$SO_2N(CH_2CH_2OH)_2$ | —$CH_3$ | 190 |
| (117) | —$SO_2N$-morpholino | —$CH_3$ | 235 |
| (118) | —$SO_3H$ | —n-$C_4H_9$ | 330 (decomposition) |
| (119) | —$SO_2N(CH_3)_2$ | —$C_6H_5$ | 193 |
| (120) | —$SO_2N(CH_3)_2$ | —$CH_2$—$C_6H_5$ | 175 |
| (121) | —$SO_2NHC_2H_5$ | —$C_2H_5$ | 217 |
| (122) | —$SO_2NH$—cyclohexyl | —cyclohexyl | 224 |
| (123) | —$SO_2NH_2$ | —$CH_2C_6H_5$ | 257 |
| (124) | —$SO_2NHCH_3$ | —n-$C_4H_9$ | 220 |
| (125) | —$CF_3$ | —$CH_3$ | 150 |
| (126) | —$SO_2NH$—$CH_2CH_2OCH_3$ | —$CH_2CH_2OCH_3$ | 159 |
| (127) | —$SO_2NH_2$ | —n-$C_4H_9$ | 240 |
| (128) | —$SO_2NHCH_2CH=CH_2$ | —$CH_2CH=CH_2$ | 174 |
| (129) | —COOH | —$CH_2$—$C_6H_5$ | 250 |
| (130) | —$SO_2NH$—$CH_2CH_2OCH_3$ | —$CH_3$ | 218 |

TABLE II-continued

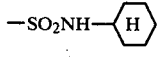

(102)

| formula | $R_5$ | $R_7$ | m.p. |
|---|---|---|---|
| (131) | —$SO_2NHC_6H_5$ | —$CH_3$ | 299 |
| (132) | —$SO_2NHCH_3$ | —$CH_2$—$C_6H_5$ | 242 |
| (133) | —$CONH_2$ | —$CH_2$—$C_6H_5$ | 210 |
| (134) | —$SO_2NH$—$CH_2C_6H_5$ | —$CH_2$—$C_6H_5$ | 232 |
| (135) | —$SO_2OC_6H_5$ | —$CH_2$—$C_6H_5$ | 142 |
| (136) | —$SO_2NH_2$ | —$C_2H_5$ | 305 |
| (137) | —$SO_2OC_6H_4$—o-$CH_3$ | —$CH_3$ | 170 |
| (138) | —$SO_2OC_6H_5$ | —$C_2H_5$ | 148 |
| (139) | —$CF_3$ | —$CH_2$—$C_6H_5$ | 144 |

The purification of the compound of the formula (112) is effected via the ammonia salt by dissolving the sparingly soluble inner salt of the sulphonic acid in boiling n-propanol by adding conc. ammonia and, after clear filtration using activated charcoal, precipitating it again with glacial acetic acid and conc. hydrochloric acid.

The compound of the formula (114) is isolated by completely concentrating the reaction solution from which the product cannot be precipitated with water and stirring the oily residue at room temperature in 1 N aqueous sodium hydroxide solution, whereupon the product precipitates. After neutralisation with hydrochloric acid to pH 6, the batch is boiled briefly and working up is performed in the usual manner.

The compound of the formula (115) is isolated by completely concentrating the reaction mixture in vacuo, dissolving the residue in boiling water, precipitating the free base with conc. aqueous ammonia and working up in the usual manner.

The compound of the formula (116) is isolated by completely concentrating the reaction mixture in vacuo, dissolving the residue in boiling n-propanol and adding 20% aqueous sodium hydroxide solution until weakly basic reaction takes place, whereupon the product crystallises on cooling.

The compound of the formula (118) is isolated by completely concentrating the reaction mixture in vacuo, dissolving the residue in boiling water and precipitating the product with conc. hydrochloric acid.

EXAMPLE 2

Dimethyl sulphate (3.3 ml) is added dropwise at 120° C. to a solution of 11.1 g of the compound of the formula (101) in 30 ml of dimethyl formamide. When the dropwise addition is complete, the reaction mixture is stirred for ½ hour at this temperature, cooled, and diluted with 30 ml of isopropanol. The crystallised product is filtered off, washed three times with isopropanol and dried in vacuo, affording 12.2 g (82.2% of theory) of the quaternary benzofuranyl-benzimidazole of the formula

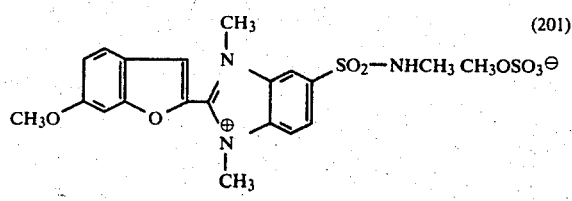

in the form of brilliant light yellow crystals with an unsharp melting point of 215° C. The compound can be used direct for optically brightening polyacrylonitrile substrates or it can be recrystallised from water beforehand to yield brilliant light yellow crystals with unchanged melting point.

The compounds of the general formula (202) listed in Table III are obtained in similar manner from the compounds of Table II and corresponding quaternising agents of the formula $R_8$-X. The melting points are generally very unsharp and are sometimes dependent on the solvent used for recrystallisation.

TABLE III

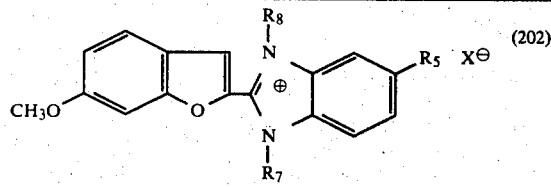

| formula | $R_5$ | $R_7$ | $R_8$ | X | melting point |
|---|---|---|---|---|---|
| (203) | —COOH | —CH₃ | —CH₃ | CH₃SO₄ | 258 |
| (204) | —SO₂N(CH₃)₂ | —CH₃ | —CH₃ | CH₃SO₄ | 199 |
| (205) | —COOC₂H₅ | —CH₃ | —CH₃ | CH₃SO₄ | 151 |
| (206) | —SO₂NH₂ | —CH₃ | —CH₃ | CH₃SO₄ | 218 |
| (207) | —CONHCH₃ | —CH₃ | —CH₃ | CH₃SO₄ | 221 |
| (208) | —COOH | —C₂H₅ | —CH₃ | CH₃SO₄ | 239 |
| (209) | —COOCH₃ | —CH₃ | —CH₃ | CH₃SO₄ | 212 |
| (210) | —SO₂N(C₂H₅)C₆H₅ | —CH₃ | —CH₃ | CH₃SO₄ | 175 |
| (211) | —CN | —CH₃ | —CH₃ | CH₃SO₄ | 257 |
| (212) | —SO₃⊖ | —CH₃ | —CH₃ | — | >360 |
| (213) | —SO₂OC₆H₅ | —CH₃ | —CH₃ | CH₃SO₄ | 205 |
| (214) | —SO₂N(CH₃)₂ | —CH₃ | —CH₂C₆H₅ | Br | 224 |
| (215) | —SO₂N(CH₃)₂ | —CH₃ | —C₂H₅ | C₂H₅SO₄ | 173 |
| (216) | —SO₂NHCH₂CH₂OH | —CH₂CH₂OH | —CH₃ | J | 200 |
| (217) | —SO₂N(CH₂CH₂OH)₂ | —CH₃ | —CH₃ | J | 220 |
| (218) | —SO₂N(morpholino) | —CH₃ | —CH₃ | CH₃SO₄ | 183 |
| (219) | —SO₃⊖ | —n-C₄H₉ | —CH₃ | — | 200 |
| (220) | —SO₂N(CH₃)₂ | —C₆H₅ | —CH₃ | CH₃SO₄ | 175 |
| (221) | —SO₂N(CH₃)₂ | —CH₂C₆H₅ | —CH₃ | CH₃SO₄ | 195 |
| (222) | —SO₂N(CH₃)₂ | —CH₃ | —CH₂COOC₂H₅ | Br | 201 decomposition |
| (223) | —SO₂N(CH₃)₂ | —CH₃ | —CH₃ | CH₃—C₆H₄—SO₃ | 222 |
| (224) | —SO₂NHC₂H₅ | —C₂H₅ | —CH₃ | CH₃SO₄ | 93 |
| (225) | —SO₂NH—C₆H₁₁ | —C₆H₁₁ | —CH₃ | CH₃SO₄ | 170 |
| (226) | —SO₂NH₂ | —CH₂C₆H₅ | —CH₃ | CH₃SO₄ | 245 |
| (227) | —SO₂N(CH₃)₂ | —CH₃ | —CH₂CH=CH₂ | Br | 150 |
| (228) | —SO₂N(CH₃)₂ | —CH₃ | —CH₂CN | Cl | 258 |
| (229) | —SO₂N(CH₃)₂ | —CH₃ | —CH₂CONH₂ | Cl | 241 |
| (230) | —SO₂NHCH₃ | —n-C₄H₉ | —CH₃ | CH₃SO₄ | 123 |

TABLE III-continued (Structure 202: 6-methoxybenzofuran with =N-R8, quaternised nitrogen bonded to phenyl ring bearing R5, and N-R7, X⁻ counterion)

| formula | R5 | R7 | R8 | X | melting point |
|---|---|---|---|---|---|
| (231) | —CF₃ | —CH₃ | —CH₃ | CH₃SO₄ | 237 |
| (232) | —SO₂NH₂ | —n-C₄H₉ | —CH₃ | CH₃SO₄ | 207 |
| (233) | —SO₂NHCH₂CH₂OCH₃ | —CH₂CH₂OCH₃ | —CH₃ | CH₃SO₄ | 103 |
| (234) | —SO₂NHCH₂CH=CH₂ | —CH₂CH=CH₂ | —CH₃ | CH₃SO₄ | 85 |
| (235) | —COOH | —CH₂C₆H₅ | —CH₃ | CH₃SO₄ | 251 |
| (236) | —SO₂NHCH₂CH₂OCH₃ | —CH₃ | —CH₃ | CH₃SO₄ | 198 |
| (237) | —SO₂NHC₆H₅ | —CH₃ | —CH₃ | CH₃SO₄ | 238 |
| (238) | —SO₂NHCH₃ | —CH₂C₆H₅ | —CH₃ | CH₃SO₄ | 184 (.H₂O) |
| (239) | —COOCH₃ | —CH₃ | —CH₂CH₂OH | Cl | 210 (.½H₂O) |
| (240) | —CONH₂ | —CH₂C₆H₅ | —CH₃ | CH₃SO₄ | 210 |
| (241) | —SO₂NHCH₂C₆H₅ | —CH₂C₆H₅ | —CH₃ | CH₃SO₄ | 216 |
| (242) | —SO₂OC₆H₅ | —CH₂C₆H₅ | —CH₃ | CH₃SO₄ | 93 |
| (243) | —SO₂NH₂ | —C₂H₅ | —CH₃ | CH₃SO₄ | 183 |
| (244) | —SO₂OC₆H₄—o-CH₃ | —CH₃ | —CH₃ | CH₃SO₄ | 103 |
| (245) | —SO₂OC₆H₅ | —C₂H₅ | —CH₃ | CH₃SO₄ | 177 |
| (246) | —CF₃ | —CH₂C₆H₅ | —CH₃ | CH₃SO₄ | 195 |

If the quaternisation is not carried out in dimethyl formamide at 120° C., the solvents and temperatures listed in Table IV are used. The other reaction conditions correspond to those indicated at the start of this Example.

TABLE IV

| Solvent | Temperature | Compound of the formula |
|---|---|---|
| dioxane | reflux | (210), (213), (215), (231), (233), (234), (240), (242), (244), (245), (246) |
| xylene | 120° C. | (209) |
| benzyl bromide | 140° C. | (214) |
| anisole | 100° C. | (217) |
| anisole | 120° C. | (236) |
| bromethyl acetate | 100° C. | (222) |
| chlorobenzene | 110° C. | (218) |
| chlorobenzene | 120° C. | (220), (221), (223), (225), (227) |
| chlorobenzene | reflux | (229) |
| chloracetonitrile | reflux | (228) |
| dioxane/anisole/dimethyl formamide | reflux | (206), (224) |
| dimethyl formamide chlorobenzene/ | 120° C. | (226), (238), (241) |
| dimethyl formamide | 120° C. | (230) |
| ethylenechlorohydringe | reflux | (239) |

When using dimethyl formamide mixtures, dimethyl formamide is always added to the other solvent until the starting material just dissolves at the desired temperature. The quaternisation product often precipitates at elevated temperature.

A substantial excess of quaternising agent (methyl iodide, allyl bromide, chloroacetamide) is used in the manufacture of the compounds of the formulae (216), (217), (227) and (229).

To manufacture the compound of the formula (212), the sparingly soluble starting material of the formula (112) is first dissolved by addition of the stoichiometric amount of triethanolamine at room temperature in dimethyl formamide (formation of the sulphonic acid triethanolamine salt) and, after addition of dimethyl sulphate, heated to 60° C. and then to 110° C., in the course of which the reaction product precipitates.

The compound of the formula (118) is obtained in the same way from the compound of the formula (219), except that anhydrous sodium acetate is used instead of triethanolamine (formation of the sodium salt of the sulphonic acid). When the reaction is complete, the reaction product precipitates upon addition of conc. hydrochloric acid.

If a quaternisation product does not precipitate from the reaction mixture, or precipitates only in the form of an oil, the reaction mixture is completely concentrated in vacuo and the residue is crystallised from a suitable solvent, such as water, n-propanol or mixtures thereof.

EXAMPLE 3

Hydrogen chloride is introduced into a solution of 3.7 g of the compound of the formula (101) in 150 ml of chlorobenzene and 30 ml of dimethyl formamide at reflux temperature until saturation is attained, whereupon a yellow product precipitates. This product is collected by suction, washed repeatedly with alcohol and dried in a high vacuum at 120° C., giving 4.4 g of the compound of the formula

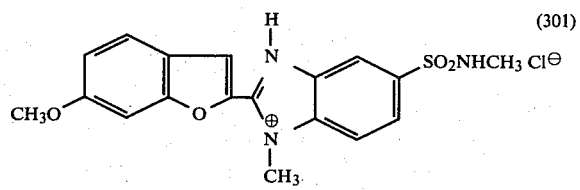

(301)

with a melting point of 247° C.

EXAMPLE 4

10 g of 6-n-butoxy-benzofurane-2-carboxylic acid are refluxed for 1 hour in 4.1 ml of thionyl chloride, 30 ml of toluene and 0.4 ml of dimethyl formamide. The solution is completely concentrated in vacuo and the residue is reacted in accordance with Example 1 with 9.2 g of 3-amino-4-methylaminobenzene-methylsulphonamide, affording 15.6 g of the compound of the formula

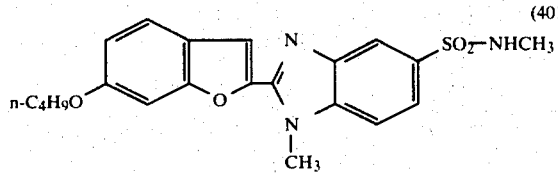
(401)

which, after recrystallisation from chlorobenzene, melts at 256° C.

The compounds of the formulae

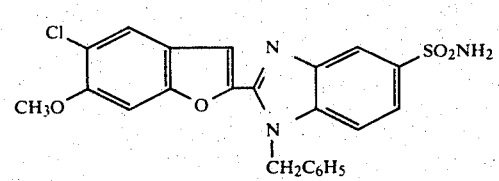
(402)

(melting point: 302° C.)

and

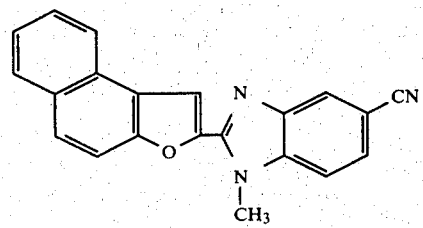
(403)

(melting point: 283° C.)

are obtained in analogous manner from 5-chloro-6-methoxybenzofurane-2-carboxylic acid and 4,5-benzocoumarone-2-carboxylic acid respectively and the corresponding o-phenylenediamines.

EXAMPLE 5

Quaternisation of the compounds of the formulae (401), (402) and (403) with dimethyl sulphate in 110 ml of anisole/dimethyl formamide at 120° C. in accordance with Example 2 yields the compounds of the formulae

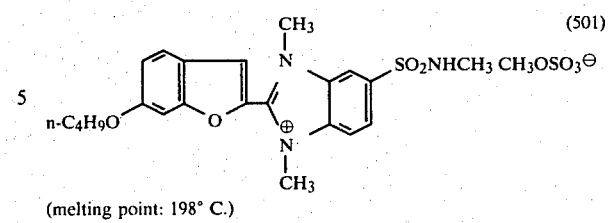
(501)

(melting point: 198° C.)

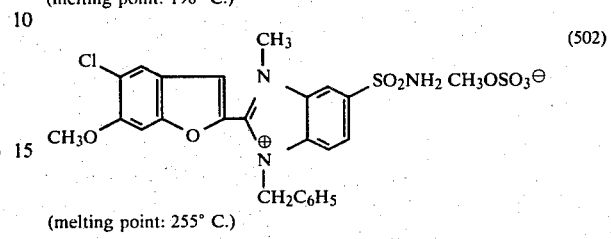
(502)

(melting point: 255° C.)

and

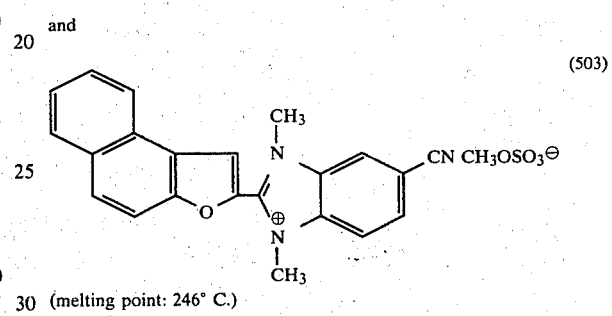
(503)

(melting point: 246° C.)

EXAMPLE 6 AND 7

Repetition of the method described in Example 1 using the corresponding amounts of respectively required starting materials gives the compounds of the formula (600; n=0) listed in Table V. Reaction of these compounds in accordance with the particulars of Example 2 with dimethyl sulphate gives the corresponding quaternised compounds of the formula (700; n=1) also listed in Table V.

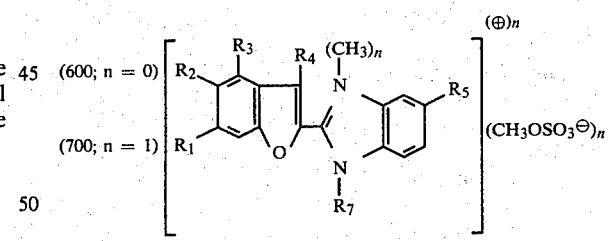

TABLE V

| formula | | | | | | | |
|---|---|---|---|---|---|---|---|
| n = 0 | n = 1 | $R_5$ | $R_7$ | $R_4$ | $R_3$ | $R_2$ | $R_1$ |
| (601) | (701) | —SO$_2$NHCH$_3$ | CH$_3$ | CH$_3$ | H | H | OCH$_3$ |
| (602) | (702) | —SO$_2$NHCH$_3$ | CH$_3$ | OCH$_3$ | H | H | OCH$_3$ |
| (603) | (703) | —SO$_2$NHCH$_3$ | CH$_3$ | H | —CH=CH—CH=CH— | | H |
| (604) | (704) | —SO$_2$NH$_2$ | CH$_3$ | H | —CH=CH—CH=CH— | | H |
| (605) | (705) | —COOH | CH$_3$ | H | —CH=CH—CH=CH— | | H |
| (606) | (706) | —COOCH$_3$ | CH$_3$ | H | —CH=CH—CH=CH— | | H |
| (607) | (707) | —CN | CH$_3$ | H | —CH=CH—CH=CH— | | H |
| (608) | (708) | —CONH$_2$ | CH$_3$ | H | —CH=CH—CH=CH— | | H |
| (609) | (709) | —CONHCH$_3$ | CH$_3$ | H | —CH=CH—CH=CH— | | H |
| (610) | (710) | —SO$_2$OC$_6$H$_5$ | CH$_3$ | H | —CH=CH—CH=CH— | | H |
| (611) | (711) | —CF$_3$ | CH$_3$ | H | —CH=CH—CH=CH— | | H |
| (612) | (712) | —SO$_2$NHCH$_2$CH$_2$OCH$_3$ | CH$_3$ | H | —CH=CH—CH=CH— | | H |
| (613) | (713) | —SO$_2$NHCH$_2$—CH=CH$_2$ | CH$_3$ | H | H | H | OCH$_3$ |
| (614) | (714) | —SO$_2$NH—n-C$_3$H$_7$ | n-C$_3$H$_7$ | H | H | H | OCH$_3$ |
| (615) | (715) | —SO$_2$NH—CH(CH$_3$)$_2$ | CH$_3$ | H | H | H | OCH$_3$ |

TABLE V-continued

| formula n=0 | n=1 | R5 | R7 | R4 | R3 | R2 | R1 |
|---|---|---|---|---|---|---|---|
| (616) | (716) | —SO$_2$NH(CH$_2$)$_3$OCH(CH$_3$)$_2$ | CH$_3$ | H | H | H | OCH$_3$ |
| (617) | (717) | —SO$_2$NH—(CH$_2$)$_3$OCH$_3$ | CH$_3$ | H | H | H | OCH$_3$ |
| (618) | (718) | —COOH | n-C$_4$H$_9$ | H | H | H | OCH$_3$ |
| (619) | (719) | —COOH | n-C$_3$H$_7$ | H | H | H | OCH$_3$ |
| (620) | (720) | —COOC$_6$H$_5$ | CH$_3$ | H | H | H | OCH$_3$ |
| (621) | (721) | —COOC$_6$H$_4$—o-CH$_3$ | CH$_3$ | H | H | H | OCH$_3$ |
| (622) | (722) | —COO—⟨H⟩ | CH$_3$ | H | H | H | OCH$_3$ |
| (623) | (723) | —COOCH$_2$CH$_2$OCH$_3$ | CH$_3$ | H | H | H | OCH$_3$ |
| (624) | (724) | —COO—CH$_2$CH=CH$_2$ | CH$_3$ | H | H | H | OCH$_3$ |
| (625) | (725) | —COOCH$_2$C$_6$H$_5$ | CH$_3$ | H | H | H | OCH$_3$ |
| (626) | (726) | —COO—(CH$_2$)$_3$OC$_6$H$_5$ | CH$_3$ | H | H | H | OCH$_3$ |
| (627) | (727) | —COOCH$_2$CH$_2$CN | CH$_3$ | H | H | H | OCH$_3$ |
| (628) | (728) | —CONHC$_2$H$_5$ | C$_2$H$_5$ | H | H | H | OCH$_3$ |
| (629) | (729) | —CONHCH$_2$C$_6$H$_5$ | CH$_2$C$_6$H$_5$ | H | H | H | OCH$_3$ |
| (630) | (730) | —CONH—n-C$_4$H$_9$ | n-C$_4$H$_9$ | H | H | H | OCH$_3$ |
| (631) | (731) | —CONH$_2$ | n-C$_4$H$_9$ | H | H | H | OCH$_3$ |
| (632) | (732) | —CONHCH$_2$CH$_2$OCH$_3$ | CH$_3$ | H | H | H | OCH$_3$ |
| (633) | (733) | —CF$_3$ | C$_2$H$_5$ | H | H | H | OCH$_3$ |
| (634) | (734) | —CF$_3$ | n-C$_4$H$_9$ | H | H | H | OCH$_3$ |
| (635) | (735) | —CN | C$_2$H$_5$ | H | H | H | OCH$_3$ |
| (636) | (736) | —CN | n-C$_4$H$_9$ | H | H | H | OCH$_3$ |
| (637) | (737) | —CN | CH$_2$C$_6$H$_5$ | H | H | H | OCH$_3$ |
| (638) | (738) | —COOCH$_3$ | n-C$_4$H$_9$ | H | H | H | OCH$_3$ |
| (639) | (739) | —COOCH$_3$ | CH$_2$C$_6$H$_5$ | H | H | H | OCH$_3$ |
| (640) | (740) | —SO$_2$NHCH$_2$CH$_2$OH | CH$_3$ | H | H | H | OCH$_3$ |
| (641) | (741) | —SO$_2$NHCH$_3$ | CH$_3$ | H | H | H | OC$_6$H$_5$ |
| (642) | (742) | —SO$_2$NHCH$_3$ | CH$_3$ | H | H | H | OCH$_2$C$_6$H$_5$ |
| (643) | (743) | —SO$_2$NHCH$_3$ | CH$_3$ | H | H | H | OCH$_2$—CH=CH$_2$ |
| (644) | (744) | —SO$_2$NHCH$_3$ | CH$_3$ | H | H | —O—CH$_2$—O— | |
| (645) | (745) | —SO$_2$NHCH$_3$ | CH$_3$ | H | H | H | O—⟨H⟩ |
| (646) | (746) | —SO$_2$NHCH$_2$COOCH$_3$ | CH$_2$COOCH$_3$ | H | H | H | OCH$_3$ |

EXAMPLE 8

To 100 ml of water are added 0.2 g of sodium nitrate, 0.2 g of 80% sodium chlorite, 0.2 g of oxalic acid or an equivalent amount of another organic or inorganic acid suitable for this purpose. A solution of the fluorescent brightener of the formula (201) is prepared by dissolving 1 g of this compound in 1000 ml of water. Then 1.5 ml of this stock solution are added to the above solution. This liquor is heated to 60° C., then a polyacrylonitrile fabric weighing 3 g is put into it, the temperature is raised in the course of 10 to 15 minutes to 95°–98° C. and kept thereat for 60 minutes. The fabric is then rinsed in cold water and dried for 20 minutes at 60° C. The treated fabric has a strong white effect of good lightfastness. Similar effects are obtained with the compounds of the formulae (203) to (209), (211), (213) to (215), (218), (221), (222), (224), (226), (229), (230), (235), (231), (236), (238), (240), (241), (501) or (503).

Similarly good white effects are obtained by carrying out the treatment of the polyacrylonitrile fabric in the same way as described above, but without the addition of sodium chlorite and using compounds of the formulae (101), (104), (106), (108), (115), (116), (117), (120), (121), (123), (124), (126), (127), (129), (201), (203) bis (209), (211), (213) bis (215), (218), (221), (222), (224), (226), (229), (230), (231), (235), (236), (238), (240), (241), (301), (401), (403), (501), (503), (130) or (133) as fluorescent brighteners.

EXAMPLE 9

To 100 ml of water are added 0.1 g of oxalic acid, 0.1 g of sodium acetate, 0.0125 g of sodium bisulphite and 0.025 g of a polyphosphate as complexing agent. A solution of the fluorescent brightener of the formula (201) is prepared by dissolving 1 g of this compound in 1000 ml of water. Then 6 ml of this stock solution are added to the above solution. The aqueous liquor containing the fluorescent brightener is heated to 60° C. and a hank of polyacrylonitrile ("Courtelle") weighing 3 g is put into the liquor. The temperature is raised in the course of 10 to 15 minutes to 98° C. and the material is treated for 30 minutes at this temperature, then rinsed with cold water and dried. The treated material has a strong white effect of good lightfastness. Similarly good effects are obtained with the compounds of the formulae (128), (203) to (209), (211), (213) to (215), (218), (221), (222), (224), (226), (229), (230), (231), (235), (236), (238), (241), (501) and (503).

EXAMPLE 10

An aqueous solution which contains, referred to the weight of the material to be brightened, 0.3% of the fluorescent brightener of the formula (201), is prepared. This solution is warmed to 30° C. Then a modified polyester fabric prepared by cocondensation with 2 to 5 molar percent of isophthalic acid 5-sodium sulphonate (Dacron 64 ®) is put into the solution, while maintaining a liquor ratio of 1:25. The temperature is raised in the course of 30 minutes to 120° C. and kept thereat for 30 minutes. Then the bath is cooled to 80° C. in the course of 15 minutes. The fabric is then rinsed in cold water and subsequently dried at 180° C. with a flat iron. It has a strong white effect of good lightfastness. Similarly good effects are obtained with the compounds of the formulae (128), (205), (207), (208), (209), (223), (224), (226), (230), (231), (236), (240) and (501).

EXAMPLE 11

A modified polyester fabric (Dacron 64 ®) is padded at room temperature with an aqueous dispersion which contains, per liter, 1 g of a fluorescent brightener of the formula (204) and 1 g of an adduct of approx. 8 moles of ethylene oxide and 1 mole of p-tert.-octylphenol. The liquor pick-up is 60 to 70%. The fabric is dried at 100° C. and then heated for 10 seconds to 220° C. The treated fabric has a strong white effect of good lightfastness. Similarly good results are obtained with the compounds of the formulae (207), (209), (224), (230), (231), (236), (238), (240) and (501).

EXAMPLE 12

Freshly spun, stretched polyacrylonitrile wet cable (corresponding to 3 g dry weight) is immersed, while still moist, at 20° C. for 10 seconds in 100 ml of an aqueous liquor which contains 0.0005% of the fluorescent brightener of the formula (201) and has been adjusted with conc. oxalic acid solution to pH 4. The wet cable is subsequently rinsed briefly with water and dried at 90° to 100° C. Polyacrylonitrile fibres with good white effects are obtained. Similarly good effects are obtained with the compounds of the formulae (203), (204), (205), (207), (208), (209), (211), (215), (218), (222), (224), (230), (231), (236), (238), (240) and (501).

The brightening can also be carried out for example at pH 6 (adjusted by addition of sodium acetate). Raising the temperature of the liquor, for example to 40° C., increases the rate of exhaustion.

Stronger white effects are obtained by increasing the brightener concentration for example to 0.005%.

EXAMPLE 13

A cellulose acetate fabric is put at 50° C. into an aqueous bath which contains 0.15% of the compound of the formula (128), referred to the weight of the fabric. The liquor ratio is 1:30 to 1:40. The temperature of the treatment bath is raised to 90°–95° C. and kept thereat for 30 to 40 minutes. After rinsing and drying the fabric, a good white effect is obtained. Similarly good effects are obtained with the compounds of the formulae (201), (204), (205), (209), (211), (213) to (216), (218), (221), (223), (226), (231), (236), (238), (240), (241), (501) and (503).

EXAMPLE 14

A polyamide 6 fabric is put wet at 30° C. into an aqueous bath of pH 9 which contains 0.2% of the compound of the formula (201), referred to the weight of the fabric. The liquor ratio is 1:30. The temperature is raised to 60° C. in the course of 10 minutes and kept thereat for 20 minutes. After rinsing and drying, the treated fabric is ironed at 180° C. It has a very good white effect. Similarly good effects are obtained with the compounds of the formulae (204) to (207), (209), (211), (213) to (218), (221), (223), (224), (227), (230), (231), (234), (236), (238), (241), (501) and (502).

EXAMPLE 15

1 g of the fluorescent brightener of the formula (205) is dissolved in 1000 ml of water and 2 ml of this solution are added to a solution of 0.2 g of sodium tripolyphosphate in 100 ml of water. This brightener solution is heated to 60° C., then 3 g of cotton fabric are put into it and treated for 30 minutes at this temperature. The fabric is then rinsed for 2 minutes in running cold water and subsequently dried for 20 minutes at 60° C. The treated fabric has a strong white effect. Similarly good white effects are obtained with the compounds of the formulae (207), (209) and (240).

EXAMPLE 16

1 g of the fluorescent brightener of the formula (208) is dissolved in 100 ml of water and 20 ml of this solution are diluted with 80 ml of water. A prebleached cotton fabric is padded with this solution at room temperature (liquor pick-up 60 to 70%). The fabric is then immediately dried at 160° C. for 20 seconds. The treated fabric has a strong white effect. Similarly good effects are obtained with the compounds of the formulae (223), (224), (230), (233), (234), (236) and (240).

EXAMPLE 17

50 g of bleached cellulose (10% suspension, approx. pH 7, unsized) are mixed in a mixer beaker with 1000 ml of softened water and 10 ml of a 0.5% solution of a fluorescent brightener of the formula (209). The mixing procedure is continued for a further minute. The pulp is then processed in known manner to paper sheets which are subsequently pressed and dried. The paper has a strong white effect.

EXAMPLE 18

2 g of a fluorescent brightener of the formula (209) are dissolved in 50 ml of hot distilled water of 90° C. Then a colloidal solution of 80 g of a degraded starch in 1000 ml of hot water of 90° C. is prepared. The brightener solution is then added to the starch solution and the resultant solution can have a pH value of 5.5 to 7.

A sized printing paper is surface-coated in a size press with this liquor and the coated paper is dried at approx. 90° to 120° C. in the drying compartment of the paper machine. A paper having a very high degree of whiteness is obtained.

Instead of sized paper it is also possible to use sized cardboard with equal success.

EXAMPLE 19

A homogeneous mixture of 65 parts of polyvinyl chloride (suspension type), 32 parts of dioctyl phthalate, 3 parts of of an epoxidised soya bean oil, 1.5 parts of a stabiliser (e.g. Irgastab BC 26 ®), 0.5 part of costabiliser (e.g. Irgastab CH 300 ®), 5 parts of $TiO_2$ (rutile type) and 91 parts of a compound of the formula (205), (209) or (221) are rolled to a sheet at 150° C. on a calender. The sheet has a strong white effect.

What we claim is:

1. A benzofuranyl-benzimidazole of the formula

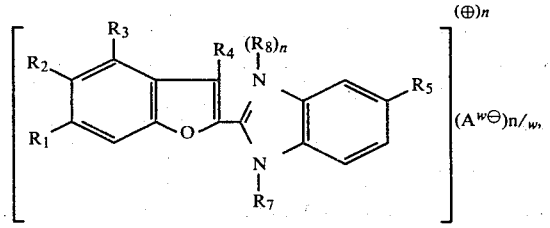

wherein
R₁ represents alkoxy of 1 to 12 carbon atoms, alkenyloxy of 3 or 4 carbon atoms, phenoxy or phenylalkoxy containing 1 to 4 carbon atoms in the alkoxy moiety which is unsubstituted or substituted in the phenyl moiety by chlorine, alkyl or alkoxy, each of 1 to 4 carbon atoms, or represents hydroxy-($C_1$-$C_4$)-alkoxy, ($C_1$-$C_4$)-alkoxy-($C_1$-$C_4$)-alkoxy, cyano-($C_1$-$C_4$)-alkoxy, carb-($C_1$-$C_4$)-alkoxy-($C_1$-$C_4$)-alkoxy, carbamoyl-($C_1$-$C_4$)-alkoxy or cyclohexyloxy or represents hydrogen if R₂ and R₃ together form butadienylene, or together with R₂ forms methylenedioxy or ethylenedioxy, R₂ represents a hydrogen or halogen atom, alkyl or alkoxy, each of 1 to 4 carbon atoms, or, if R₁ represents hydrogen, together with R₃ forms butadienylene, or together with R₁ forms methylenedioxy or ethylenedioxy, R₃ represents a hydrogen atom, alkyl or alkoxy, each of 1 to 4 carbon atoms, or, if R₁ represents hydrogen, together with R₂ forms butadienylene, R₄ represents hydrogen, alkyl or alkoxy, each of 1 to 4 carbon atoms, or phenyl, R₇ represents alkyl of 1 to 8 carbon atoms, alkenyl of 3 to 4 carbon atoms, cyclohexyl, hydroxyalkyl of 2 to 4 carbon atoms, alkoxyalkyl of altogether 3 to 6 carbon atoms, carboxyalkyl of 2 to 5 carbon atoms, carbalkoxyalkyl of altogether 3 to 9 carbon atoms, cyanoalkyl of 2 to 5 carbon atoms, benzyl which is unsubstituted or substituted by chlorine, methyl or methoxy; dialkylaminoalkyl of altogether 3 to 7 carbon atoms or phenethyl, or, if n is 0, also represents hydrogen, R₈ represents hydrogen, alkyl or 1 to 6 carbon atoms, hydroxyalkyl of 2 to 4 carbon atoms, cyanoalkyl of 2 to 5 carbon atoms, carboxyalkyl of 2 to 5 carbon atoms, carbamoylalkyl of 2 to 6 carbon atoms, alkoxycarbonylalkyl of altogether 3 to 9 carbon atoms, alkenyl of 3 to 4 carbon atoms, or benzyl which is unsubstituted or substituted by chlorine, methoxy or methyl, R₅ represents cyano or trifluoromethyl, n is 0 or 1, $A^{w\ominus}$ represents a colourless anion and w represents the valency of the anion A.

2. A benzofuranyl-benzimidazole as defined in claim 1 wherein
R₁ represents alkoxy of 1 to 8 carbon atoms, alkenyloxy of 3 to 4 carbon atoms, benzyloxy or phenoxy, alkoxyalkoxy of altogether 3 to 6 carbon atoms, or represents a hydrogen atom if R₂ and R₃ together forms butadienylene, R₂ represents a hydrogen or chlorine atom or, if R₁ represents hydrogen, together with R₃ forms butadienylene, R₃ represents a hydrogen atom or together with R₂ forms butadienylene, R₄ represent a hydrogen atom, R₅ represents cyano or trifluoromethyl, R₇ represents alkyl of 1 to 6 carbon atoms, alkenyl of 3 or 4 carbon atoms, cyclohexyl, hydroxyalkyl of 2 to 4 carbon atoms, alkoxyalkyl of altogether 3 to 6 carbon atoms, carbalkoxyalkyl of altogether 3 to 6 carbon atoms or benzyl, and, if n is 0, also represents hydrogen, R₈ represents hydrogen, alkyl of 1 to 4 carbon atoms which is unsubstituted or substituted by hydroxy, cyano, carboxy, alkoxycarbonyl of 2 to 4 carbon atoms or carbamoyl, or represents alkenyl of 3 or 4 carbon atoms or benzyl, n is 0 or 1, $A^{w\ominus}$ represents a halide, formate, acetate, lactate, $CH_3SO_4^{\ominus}$, $C_2H_5SO_4^{\ominus}$, $C_6H_5SO_3^{\ominus}$, p—$CH_3$—$C_6H_4SO_3^{\ominus}$, p—Cl—$C_6H_4SO_3^{\ominus}$, carbonate or bicarbonate and w represents the valency of the anion A.

3. A benzofuranyl-benzimidazole as defined in claim 1 wherein
R₁ represents alkoxy of 1 to 4 carbon atoms or, if R₂ and R₃ together forms butadienylene, R₁ represents a hydrogen atom, R₂ represents a hydrogen or chlorine atom or together with R₃ forms butadienylene if R₁ represents hydrogen, R₃ represents a hydrogen atom or together with R₂ forms butadienylene if R₁ represents hydrogen, R₄ represents a hydrogen atom, R₅ represents cyano or trifluoromethyl, R₇ represents alkyl of 1 to 6 carbon atoms or benzyl, R₈ represents hydrogen, alkyl of 1 to 4 carbon atoms, carbalkoxy of altogether 3 to 5 carbon atoms or benzyl, $A^{w\ominus}$ represents a halogen ion or a methylsulphate, ethylsulfate or p-tolylsulphate ion, and n and w are as defined in claim 1.

4. A benzofuranyl-benzimidazole as defined in claim 1 wherein
R₁ represents alkoxy of 1 to 4 carbon atoms, R₂, R₃ and R₄ each represent a hydrogen atom, RHD 5 represents cyano or trifluoromethyl, R₇ represents alkyl of 1 to 6 carbon atoms or benzyl, R₈ represents hydrogen, alkyl of 1 to 4 carbon atoms, carbalkoxyalkyl of altogether 3 to 6 carbon atoms or benzyl, $A^{\ominus}$ is a halogen, methylsulfate, ethylsulfate or p-tolylsulfate ion, and n and w are each 1.

5. A benzofuranyl-benzimidazole as defined in claim 1 wherein
R₁ represents alkoxy of 1 to 4 carbon atoms, R₂, R₃ and R₄ each represent a hydrogen atom, R₅ represents cyano or trifluoromethyl, R₇ represents alkyl of 1 to 4 carbon atoms, alkoxyalkyl of altogether 3 to 6 carbon atoms or benzyl, and n is 0.

* * * * *